United States Patent
Homan et al.

(10) Patent No.: US 11,007,014 B2
(45) Date of Patent: May 18, 2021

(54) MEDICAL INSTRUMENT TRACKING

(71) Applicant: KONINKLIJKE PHILIPS N.V., Eindhoven (NL)

(72) Inventors: Robert Johannes Frederik Homan, Best (NL); Ronaldus Frederik Johannes Holthuizen, Odijk (NL); Michael Grass, Buchholz in der Nordheide (DE); Harold Agnes Wilhelmus Schmeitz, Eindhoven (NL); Bernardus Hendrikus Wilhelmus Hendriks, Eindhoven (NL); Thirukumaran Thangaraj Kanagasabapathi, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 334 days.

(21) Appl. No.: 16/062,636

(22) PCT Filed: Dec. 16, 2016

(86) PCT No.: PCT/EP2016/081346
§ 371 (c)(1),
(2) Date: Jun. 15, 2018

(87) PCT Pub. No.: WO2017/103046
PCT Pub. Date: Jun. 22, 2017

(65) Prior Publication Data
US 2020/0281660 A1    Sep. 10, 2020

(30) Foreign Application Priority Data

Dec. 18, 2015 (EP) .................................. 15201029

(51) Int. Cl.
*G06T 7/73* (2017.01)
*A61B 34/20* (2016.01)
(Continued)

(52) U.S. Cl.
CPC .............. *A61B 34/20* (2016.02); *A61B 90/92* (2016.02); *A61B 90/96* (2016.02); *G06T 7/246* (2017.01);
(Continued)

(58) Field of Classification Search
CPC ......... A61B 34/20; A61B 90/96; A61B 90/92; A61B 2034/2065; A61B 2034/2055;
(Continued)

(56) References Cited

U.S. PATENT DOCUMENTS 8,170,302 B1 * 5/2012 Gleason ............... A61B 6/5264
382/128
8,553,839 B2 10/2013 Hendriks
(Continued)

FOREIGN PATENT DOCUMENTS

EP    1952779 A1    8/2008
WO    199938449 A1    8/1999
(Continued)

*Primary Examiner* — Sheela C Chawan

(57) ABSTRACT

The present invention relates to medical instrument tracking. In order to facilitate tracking a medical instrument, a system (100) is provided for tracking a medical instrument. The system comprises an instrument marker (14), a tracking arrangement (16), and a processing unit (18). The instrument marker is attached to the medical instrument on a marker position (20). The tracking system is configured to detect line segments (22) in the 5 field of interest and to detect the attached instrument marker. The processing unit is configured to identify a line segment (24) on which the attached instrument marker is detected as the medical instrument, and to determine an offset (26) between a position of a medical instrument tip (28) and the marker (14) by touching a reference marker (34) on the subject with the medical instrument (10).

12 Claims, 4 Drawing Sheets

(51) Int. Cl.
*A61B 90/92* (2016.01)
*A61B 90/96* (2016.01)
*G06T 7/246* (2017.01)
*A61B 90/00* (2016.01)

(52) U.S. Cl.
CPC ........ *G06T 7/73* (2017.01); *A61B 2034/2055* (2016.02); *A61B 2034/2065* (2016.02); *A61B 2090/371* (2016.02); *A61B 2090/3937* (2016.02); *A61B 2090/3983* (2016.02); *G06T 2207/30204* (2013.01)

(58) Field of Classification Search
CPC ...... A61B 2090/371; A61B 2090/3937; A61B 2090/3983; G06T 7/246; G06T 7/73; G06T 2207/30204
USPC ......... 382/103, 100; 606/1, 130; 348/61, 77, 348/180, 187, 188; 702/85, 94, 127, 150
See application file for complete search history.

(56) References Cited

U.S. PATENT DOCUMENTS

| | | | |
|---|---|---|---|
| 2003/0076980 A1* | 4/2003 | Zhang | G06T 7/80 382/103 |
| 2003/0130576 A1* | 7/2003 | Seeley | A61B 6/4441 600/426 |
| 2003/0225329 A1* | 12/2003 | Rossner | A61B 90/39 600/424 |
| 2006/0264742 A1 | 11/2006 | Neubauer | |
| 2007/0173790 A1 | 7/2007 | Moctezuma De La Barrera | |
| 2008/0185430 A1 | 8/2008 | Goldbach | |
| 2012/0121124 A1* | 5/2012 | Bammer | G06T 7/248 382/103 |
| 2012/0156092 A1 | 6/2012 | Suijver | |
| 2012/0170824 A1 | 7/2012 | Hendriks | |
| 2012/0259204 A1 | 10/2012 | Carrat | |
| 2013/0315440 A1 | 11/2013 | Frank | |
| 2017/0354342 A1* | 12/2017 | Ben-Yishai | A61B 34/20 |

FOREIGN PATENT DOCUMENTS

| | | | |
|---|---|---|---|
| WO | WO-9938449 A1 * | 8/1999 | ............ A61B 90/36 |
| WO | 20030071968 A1 | 9/2003 | |
| WO | 2010067281 A1 | 6/2010 | |
| WO | 2011047467 A1 | 4/2011 | |
| WO | 2013115640 A1 | 8/2013 | |
| WO | 2014122301 A1 | 8/2014 | |
| WO | 2015032676 A1 | 3/2015 | |

* cited by examiner

MEDICAL INSTRUMENT TRACKING

CROSS-REFERENCE TO PRIOR APPLICATIONS

This application is the U.S. National Phase application under 35 U.S.C. § 371 of International Application No. PCT/EP2016/081346, filed on Dec. 16, 2016, which claims the benefit of European Patent Application No. 15201029.4, filed on Dec. 18, 2015. These applications are hereby incorporated by reference herein.

FIELD OF THE INVENTION

The present invention relates to the field of medical instrument tracking, and in particular to a system for tracking a medical instrument, to a method for tracking a medical instrument, to a computer program element, and to a computer readable medium.

BACKGROUND OF THE INVENTION

Medical instruments, such as steerable devices, flexible catheters or more rigid arms or shafts, are used in minimally invasive procedures for diagnosis and treatment of medical conditions. In certain applications and circumstances, it is valuable to know the position and orientation of the medical instruments e.g. for performing delicate procedures without damaging critical surrounding structures, such as arteries and nerves, in image guided surgical interventions. For example, WO 2015/032676 A1 describes electromagnetic tracking sensors for determining the position and shape of an interventional device.

Some tracking methods may require the information about the dimensions of the medical instruments, which may be stored in a database. For example, US 2012/0259204 A1 describes providing an instrument with visibility elements along an axis, whereby positions of the elements characterizing a specific instrument are stored in a database.

Thus, only a limited number of known medical instruments may be tracked.

SUMMARY OF THE INVENTION

There may be a need to facilitate tracking a medical instrument.

The object of the present invention is solved by the subject-matter of the independent claims, wherein further embodiments are incorporated in the dependent claims. It should be noted that the following described aspects of the invention apply also for the system for tracking a medical instrument, for the method for tracking a medical instrument, for the computer program element, and for the computer readable medium.

According to a first aspect of the present invention, a system for tracking an elongated medical instrument in a field of interest is provided. The system comprises a tracking arrangement and a processing unit.

The tracking arrangement is configured to obtain images of the medical instrument, the images including an instrument marker located on the medical instrument at a marker position remote from a tip of the medical instrument.

The processing unit is configured to i) detect at least one line segment and the instrument marker in the obtained images; ii) identify the medical instrument by selecting, from the at least one line segment detected, a line segment corresponding to the detected instrument marker; and iii) to determine an offset of a position of the tip of the medical instrument based on a the medical instrument touching a reference marker.

In an example, a straight and elongated medical instrument is used. During a medical procedure in which the instrument is being tracked, the instrument marker may be used as a reference. In order to indicate also the tip position of the medical instrument, even if part of the medical instrument is inside a subject, an offset between the marker and the tip position may be determined. For this purpose, prior to inserting the instrument into the subject, a reference marker on the subject may be touched by the instrument tip.

The touching of a reference marker by the instrument tip may be detected through the tracking arrangement. For instance, when the reference marker is visible in the images provided by the tracking arrangement, a touching between the instrument tip and the medical instrument may be detected from the images provided. Within the context of this application, "touching" shall be understood as not merely physically touching, but also virtually touching, that is, bringing the medical instrument sufficiently close to the reference marker, so that in one or more of the tracking images the instrument and marker representations overlap.

Thus, a touching may be detected even when the position of the tip of the instrument itself cannot be established in the tracking image with sufficient reliability.

In an example, at least one reference marker is provided on the subject. For instance, a set of reference markers may be provided on the exterior of a patient. In this case, the tracking arrangement may track patient movements in addition to tracking the instrument position.

In this way, there may be no need to build up a database to store the geometric information of a plurality of medical instruments. Even for an unknown device (contrary to a known medical instrument inside the database), a user can simply use an instrument marker on the medical instrument and track the medical instrument even if a part of the medical instrument is inside a subject. Thus, a broad range of medical instruments may be tracked.

The term "instrument marker located on the medical instrument" may include that the instrument marker is a separate marker attached to the medical instrument and that the instrument marker is an integral part of the medical instrument.

In an embodiment, a single instrument marker may be sufficient to track the medical instrument. The offset between a single marker and the instrument tip by be determined reliably by means of a touch interaction between the instrument tip and the reference marker.

According to an example, the instrument marker comprises at least one of the group of: a biocompatible reflective paint, a fluorescent paint, a material with intrinsic reflective response for forming the medical instrument, and a self-adhesive tape.

The instrument markers may be attached or sprayed on the medical instrument.

According to an example, the biocompatible reflective paint and/or the fluorescent paint has emission of light that is bandwidth selective.

In this way, excitation/emission of the reflective or fluorescent paint may be bandwidth selective such that a filtered light source and/or camera is used for position determination while the video image of the scene remains undisturbed.

Alternatively or in addition, a landmark of the instrument itself may be used as an instrument marker. In an example, a boundary between two portions of the instrument may be used as an instrument marker. For instance, a boundary between a shaft and a handle portion of an instrument, which boundary is perpendicular to the shaft direction, may be visible sufficiently clearly in the tracking images to enable instrument tracking. By detecting such transition, it may become possible to track the instrument without attaching a separate (artificial) marker to the device.

To track the medical instrument, in an example an optical tracking arrangement having at least one camera is employed. Thus, a 3D position of the medical instrument may be determined by using images from the at least one camera. In an example, at least two optical cameras are used in order to enable accurate 3D tracking. As an alternative or in addition, a single depth resolving camera may be employed that generates optical images enhanced with depth measurements as an input for 3D tracking.

Alternatively, it is possible to generate a 3D model of the medical instrument by using the at least two cameras and a light source. For example, it is possible to rotate the medical instrument in front the camera system and calculate a 3D model from the sequence of the images. The cameras and the light source may have specific wavelength filters suitable for the type of reflective materials used. One or more instruments used in the procedure can be identified by using different reflective materials and using filter sets of specific wavelength.

According to a second aspect of the present invention, a method is provided for tracking a medical instrument in a field of interest. The method comprises the following steps:
a) obtaining images of the medical instrument including an instrument marker located on the medical instrument at a marker position remote from a tip of the medical instrument
b) detecting, in the images, at least one line segment in the field of interest;
c) detecting the instrument marker;
d) identifying the medical instrument by selecting, from the at least one line segment detected, a line segment corresponding to the detected instrument marker; and
f) determining an offset of a position of a medical instrument tip by touching a reference marker with the medical instrument.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

The figures are only schematically illustrated and not to scale. Same reference signs refer to same or similar features throughout the figures.

DETAILED DESCRIPTION OF EMBODIMENTS

Figure 1:
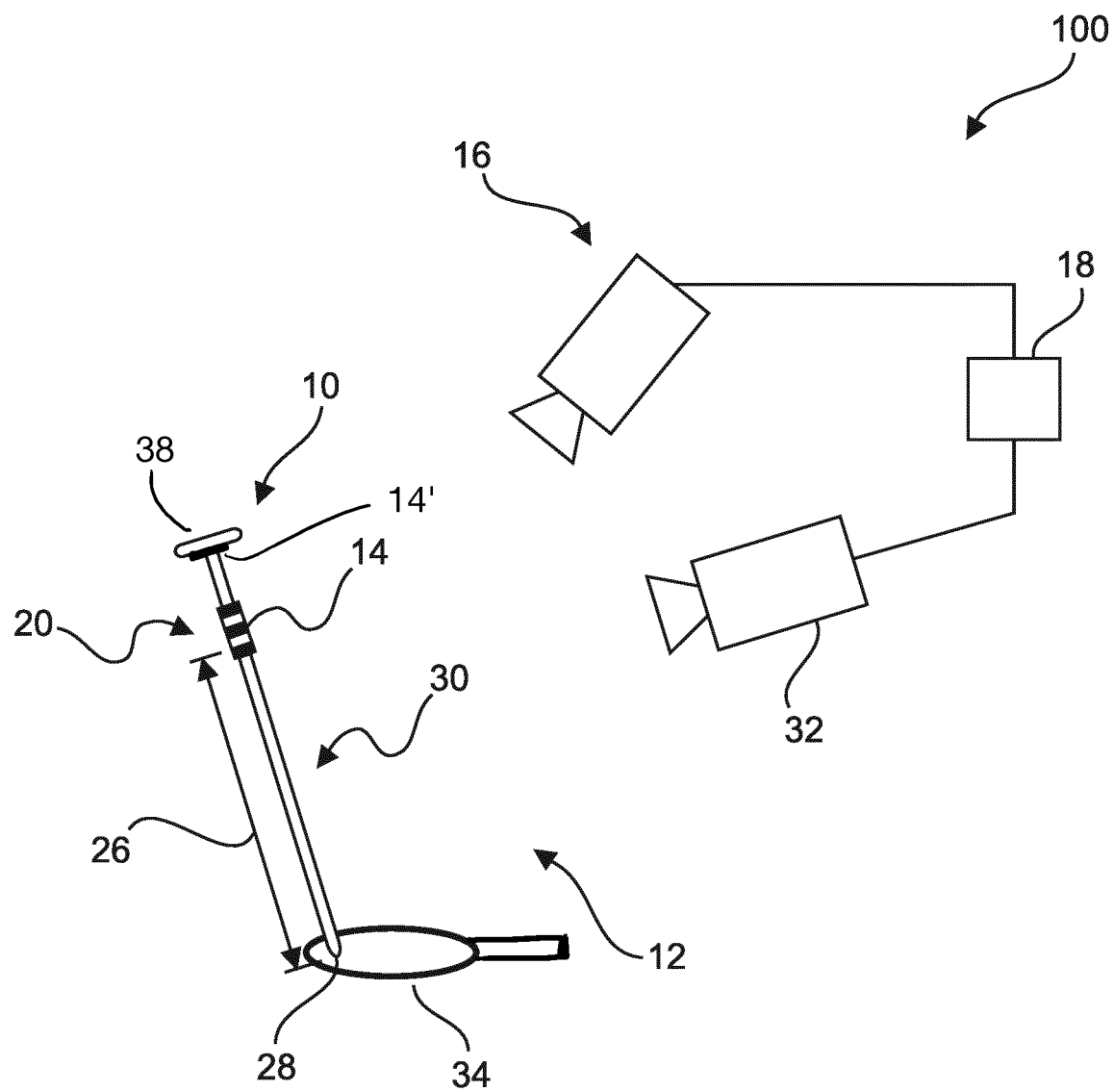
FIG. 1 schematically shows an example of a system for tracking a medical instrument.

FIG. 1 schematically shows a system 100 for tracking a medical instrument 10 in a field of interest 12.

The system 100 comprises a tracking arrangement 16, and a processing unit 18. To enable its tracking, an instrument marker 14 is located on the medical instrument 10 on a marker position 20.

The term "field of interest" may relate to a field in which the medical instrument is used, such as a surgical field, a field of operation, etc.

The term "medical instrument" may relate to a specially designed tool or device for performing specific actions of carrying out desired effects during a surgery or operation, such as modifying biological tissues.

In an example as shown in FIG. 1, the medical instrument 10 may comprise an instrument shaft 30, which is straight and elongated, and a handle 38. An instrument marker 14 is attached on the instrument shaft 30 away from a medical instrument tip 28. Alternatively or in addition, a boundary between the shaft 30 and the handle 38 may be used as an instrument marker 14'.

Thus, even if the medical instrument tip 28 is blocked, e.g. when inserted into a subject, the instrument marker 14, 14' can provide a reference for indicating the position of the medical instrument tip 28.

In an example, the instrument marker 14 comprises at least one of the group of: a biocompatible reflective paint, a fluorescent paint, a material with intrinsic reflective response for forming a part of the medical instrument, and a self-adhesive tape. Fluorescence dyes similar to those used in tumor surgeries may be used as a fluorescent paint, which should be biocompatible. Examples of fluorescence dyes include indocyanine green (ICG), fluorescein, photofrin, 5-aminolevullinic acid (ALA), patent blue, methylene blue, etc.

The biocompatible reflective paint or the fluorescent paint may be coated or sprayed on the medical instrument, such as surgical or laparoscopic instruments in use, e.g. during the minimal invasive surgical procedure.

Reflective or fluorescent dye coating may be reapplied after several usages based on the efficiency of the dye or coating material. Coating material can be autoclavable or sterilisable for repeated usage.

Alternatively, a part of the medical instrument, for example a portion of the shaft 30, may be made of a material that has intrinsic reflective or fluorescent response. In other words, a part of the medical instrument may be used as an instrument marker for indicating the position of the medical instrument tip 28.

In a further example, the instrument marker 14 is a piece of self-adhesive tape, which can be wrapped around e.g. a central axis of the medical instrument until it is securely fastened.

The self-adhesive tape may be constructed from materials including for example a silicone rubber sleeve that is slid over e.g. the medical instrument shaft, heat-shrink tubing, or a permanently painted, etched or engraved marker.

The above-mentioned instrument markers may optionally have a pattern extending in a direction for encircling the medical instrument.

In an example, as shown in FIG. 1, the instrument marker 14 has a pattern of lines. The pattern of lines, such as the number of lines and/or the thickness of the lines, may be varied to distinguish between different medical instruments. In a further example, the medical instruments with the same pattern may be distinguished between each other by using e.g. the thickness of the medical instrument shaft.

Other examples of the pattern include e.g. a 2D barcode, color code, etc. In this way, the medical instrument may be detected or tracked in all directions.

The medical instrument 10 is tracked by the tracking arrangement 16. Depending on the applications and circumstances, the tracking arrangement 16 may be an optical tracking arrangement, an ultrasonic tracking arrangement, or any other suitable tracking arrangement.

In an example, as shown in FIG. 1, the tracking arrangement 16 is an optical tracking arrangement comprising at least two optical sensors 32, such as two cameras as shown in FIG. 1, which allows for multiple medical instruments to be tracked simultaneously. The position and orientation of the optical sensors 32 relative to each other may be known, e.g. via rigid mechanical construction. As an alternative or in addition, an optical tracking arrangement may comprise a depth resolving camera providing optical images together with depth measurements.

For example, the optical sensors may be supported in a determined spatial relationship to an X-ray device in a medical imaging system, as has been described in WO 2010/067281 A1.

If reflective or fluorescent materials are used, the optical sensors 32 may comprise a wavelength filter suitable for the type of reflective or fluorescent materials used. One of more medical instruments used in the procedure may be identified by using different reflective materials and using filter sets of specific wavelengths.

The tracking system 16 may be integrated into a surgical set up either as a part of a medical imaging system (e.g. a C-arm X-ray system as stated above) or as a separate tracking unit.

In the following, to facilitate explanation of the present techniques, an optical tracking arrangement will be generally discussed herein, though it is to be understood that other tracking arrangements are also within the scope of the present techniques.

Figure 2:
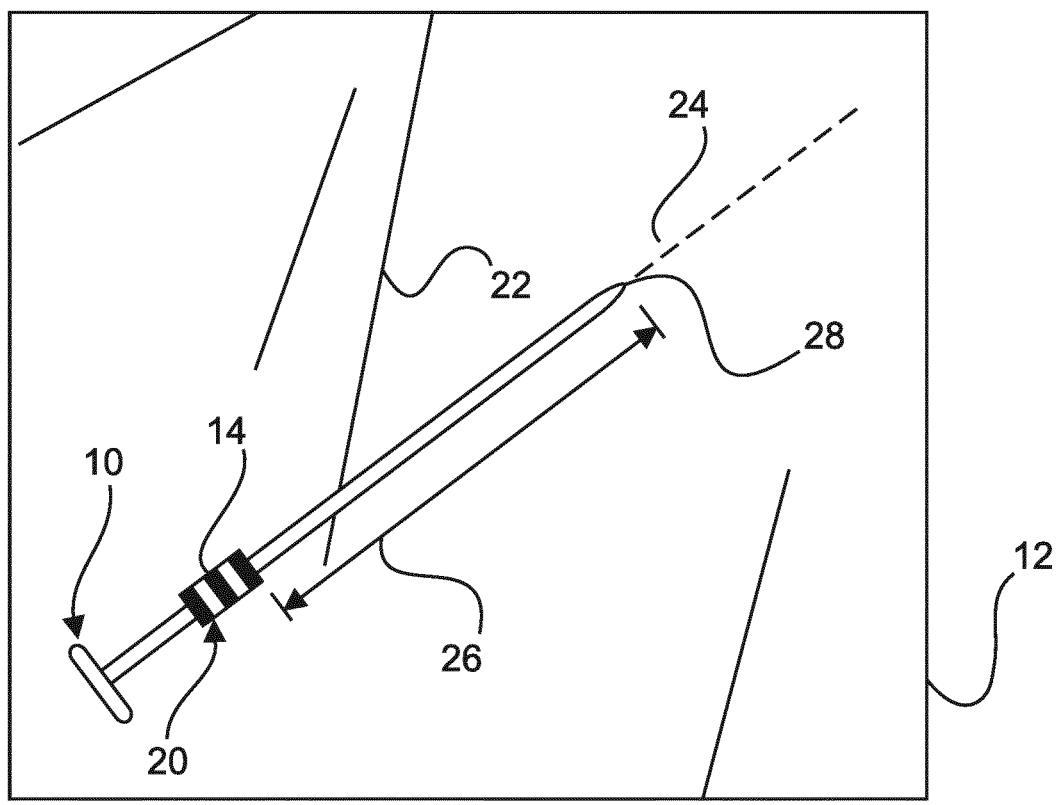
FIG. 2 schematically shows an example of a field of interest.

FIG. 2 schematically shows an example of the field of interest 12 with the medical instrument 10 inside.

The tracking system 100 is configured to detect line segments 22 (indicated with solid lines) in the field of interest 12 and to detect the instrument marker 14, or marker 14' as indicated in FIG. 1. The processing unit 18 is configured to select a line segment 24 (indicated with a dashed line) corresponding to the detected instrument marker, as the medical instrument 10, and to use the marker position 20 as a reference to determine an offset 26 of a tip position of the medical instrument tip 28.

The term "offset" relates to a spatial distance.

The tip position of the medical instrument may include possible extensions of the medical instrument, such as the length of a (rigidly) connected part, e.g. a pedicle screw attached to a screwdriver.

Now referring to both FIG. 1 and FIG. 2, during operation, the tracking system 16 images the field of interest 12 and acquires image data of the field of interest 12. The images may be corrected for lens distortion, so that straight lines in real world are visible as straight lines in the images. However, if low-distortion lenses are used, this step could be omitted.

The processing unit 18 is configured to detect straight lines in the acquired image data, e.g. via Hough transform.

The processing unit 18 is further configured to determine endpoints of each of the detected straight lines. For each detected straight line, a plane spanning the line end points and the camera center may be stored.

The processing unit 18 is further configured to determine an intersection of each pair of planes for each detected straight lines. This yields a 3D line description with a start and endpoint.

Along the detected straight line (or on the extension), the instrument marker 14 is detected on at least one camera image e.g. with pattern recognition. The straight line, on which the attached instrument marker 14 is detected, can be identified as the medical instrument and can be tracked.

When, for example, in a tracking image an overlap or intersection is detected between the tracked medical instrument 10 and a reference marker 34, that is when the instrument 10 has a distance to the reference marker 34 below a predetermined threshold, an operator can initialize the tip position. The reference marker 34 is typically a marker, within or close to the field of interest, which is used to track patient motion.

The reference marker 34 is provided to be touched by the medical instrument tip 28 and is visible in the images obtained by the tracking arrangement. The reference marker 34 may for example have a circular shape, however different shapes may be used in order to more reliably establish a touching of the marker 34 by the medical instrument tip 28. For example, the marker 34 shown in FIG. 1 has a circular body from which a tail portion extends, to further improve visibility of the marker 34 in the tracking images when an instrument 10 is adjacent to the marker.

The processing unit may further be configured to detect the distance between the instrument marker 14 and the touched reference marker 34 along the selected line segment 24, and to use the detected distance as input for determine the an offset 26 between marker 14 and tip position 28.

Alternatively, the tracking arrangement 16 is configured to acquire image data of the field of interest 12. The processing unit 18 is configured to generate a 3D model from the acquired image data and to calculate the offset 26 to the tip position based on the marker position 20.

In an embodiment (not shown), the tracking images may be made visible to a user on a display screen. In this case, feedback on a touch interaction between the instrument tip 28 and the reference marker 34 may be given in an augmented reality view. Thereby, a user can be given visual feedback that the instrument calibration has been established successfully, in other words that the tip offset has been determined. Based on this, the user may subsequently initiate an interventional procedure in which the instrument tip is inserted into the subject.

In addition, once the tip offset is initialized, a virtual instrument (not shown) may be displayed on patient data using the saved distance between the instrument marker 14 and the tip position 28 along the line segment. The patient data may be a 3D tomographic data set, which is registered prior to the minimal invasive intervention. The 3D tomographic data set may be e.g. a CT/MR (computed tomography/magnetic resonance) dataset or an XperCT/VasoCT/angiography dataset.

Figure 3:
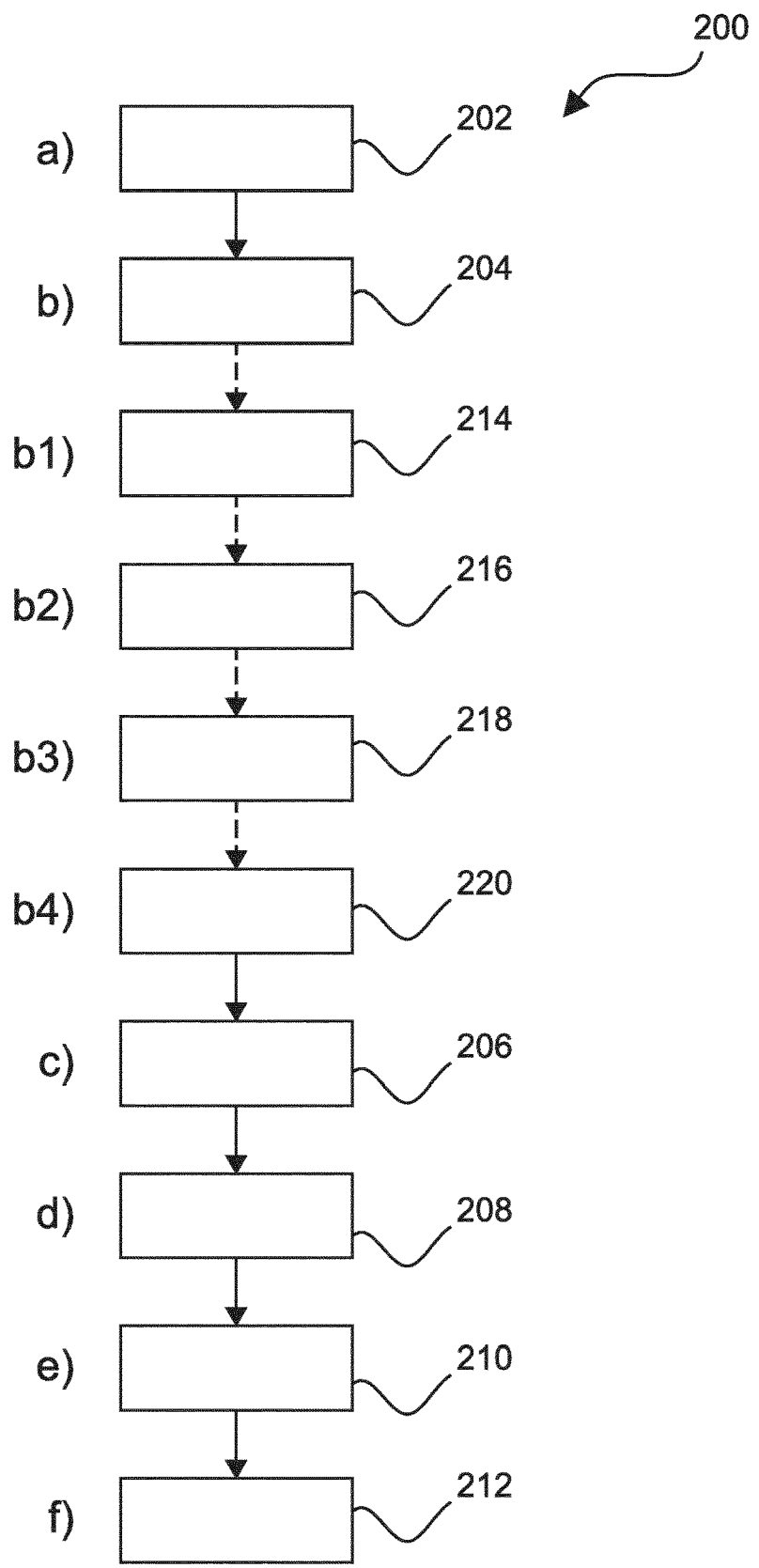
FIG. 3 shows basic steps of an example of a method for tracking a medical instrument.

Alternatively, the patient data may be live X-ray data which may be shown to a user in addition to one or more of the tracking camera images FIG. 3 shows basic steps of an example of a method 200 for tracking an instrument. The method comprises the following steps:

In a first step 202, also referred to as step a), images of the medical instrument are acquired, the images including an instrument marker located on the medical instrument at a marker position remote from a tip of the medical instrument In a second step 204, also referred to as step b), at least one line segment is detected in the images, in the field of interest In a third step 206, also referred to as step c), the instrument marker is detected.

In a fourth step 208, also referred to as step d), the medical instrument is detected by selecting, from the at least one line segment detected, a line segment corresponding to the detected instrument marker In an optional step 210, also referred to as step e), an orientation of the medical instrument is determined based on the orientation of the selected line segment.

In a fifth step 212, also referred to as step f), an offset of a position of a medical instrument tip is determined by touching a reference marker with the medical instrument.

Figure 4:
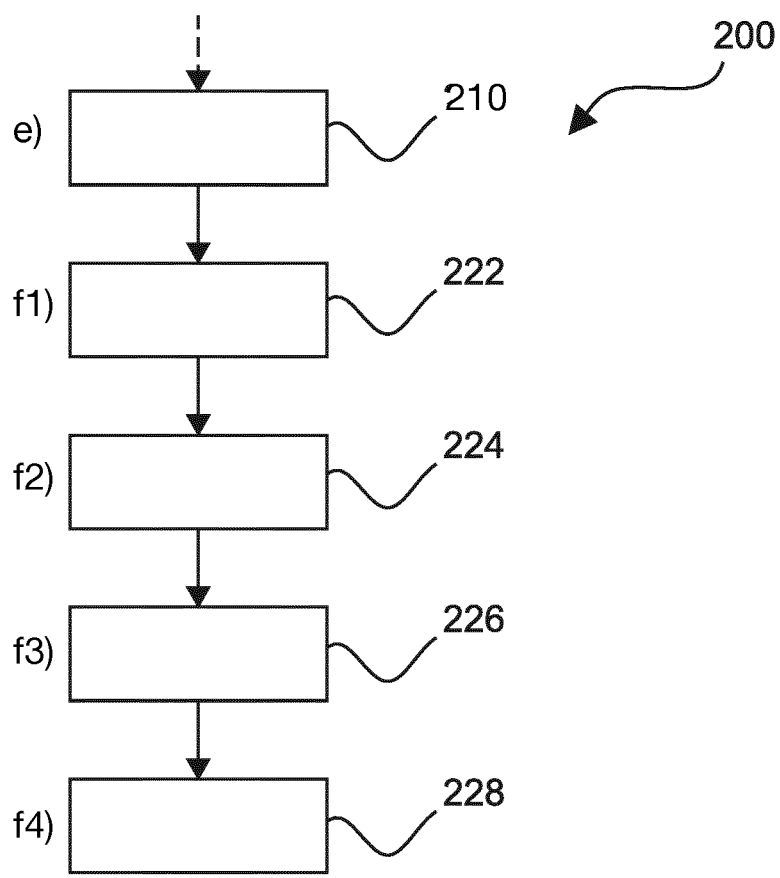
FIG. 4 shows a further example of a method.

FIG. 4 shows a further example, in which step f) of the method 200 further comprises the following sub-steps: f1) providing 222 a reference marker; f2) using 224 the medical instrument tip to touch the reference marker; f3) detecting 226 a distance between the instrument marker and the touched reference marker along the selected line segment and f4) using 228 the detected distance as the offset.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for tracking an elongated medical instrument in a field of interest, comprising:
    a tracking arrangement; and
    processing circuitry;
    wherein the tracking arrangement is configured to obtain images of the medical instrument, the images including an instrument marker located on the medical instrument at a marker position remote from a tip of the medical instrument, and
    wherein the processing circuitry is configured to:
        i) detect line segments in the field of interest in the obtained images and detect the instrument marker in the obtained images;
        ii) identify the medical instrument by selecting, from the line segments detected, a line segment corresponding to the detected instrument marker; and
        iii) to determine an offset of a position of the tip of the medical instrument based on the medical instrument touching a reference marker.

2. The system for tracking as claimed in claim 1, wherein the processing circuitry is further configured to detect a distance between the instrument marker and the touched reference marker along the selected line segment, and to use the detected distance in determining the offset.

3. The system for tracking as claimed in claim 1, wherein the instrument marker comprises at least one of the group of:
    a biocompatible reflective paint;
    a fluorescent paint;
    a material with intrinsic reflective response for forming the medical instrument; and
    a self-adhesive tape.

4. The system for tracking as claimed in claim 3, wherein the biocompatible reflective paint and/or the fluorescent paint has emission of light that is bandwidth selective.

5. The system for tracking as claimed in claim 1, wherein the instrument marker has a pattern extending in a tangential direction along a surface of the medical instrument.

6. The system for tracking as claimed in claim 1, wherein the instrument marker comprises a boundary between two portions of the instrument.

7. The system for tracking as claimed in claim 6, wherein the instrument marker is a boundary between a shaft and a handle of a needle.

8. The system for tracking as claimed in claim 7, wherein the tracking arrangement is configured to acquire image data of the field of interest; and
wherein the processing circuitry is configured to generate a 3D model from the acquired image data and to calculate the offset to the tip position based on the marker position.

9. The system for tracking as claimed in claim 8, wherein the tracking arrangement is an optical tracking system comprising at least one camera.

10. A method for tracking a medical instrument in a field of interest, comprising:
obtaining images of the medical instrument including an instrument marker located on the medical instrument at a marker position remote from a tip of the medical instrument;
detecting, in the images, line segments in the field of interest;
detecting the instrument marker;
identifying the medical instrument by selecting, from the line segments detected, a line segment corresponding to the detected instrument marker; and
determining an offset of a position of a medical instrument tip by touching a reference marker with the medical instrument.

11. The method for tracking as claimed in claim 10, further comprising:
providing a reference marker;
using the medical instrument tip to touch the reference marker;
detecting a distance between the instrument marker and the touched reference marker along the selected line segment; and
using the detected distance as the offset.

12. A non-transitory computer-readable storage medium having stored a computer program comprising instructions which, when the program is executed by a computer, cause the computer to:
obtain images of the medical instrument including an instrument marker located on the medical instrument at a marker position remote from a tip of the medical instrument;
detect, in the images, line segments in the field of interest;
detect the instrument marker;
identify the medical instrument by selecting, from the line segments detected, a line segment corresponding to the detected instrument marker; and
determine an offset of a position of a medical instrument tip by touching a reference marker with the medical instrument.

* * * * *